United States Patent [19]

Huang et al.

[11] Patent Number: 4,482,753

[45] Date of Patent: Nov. 13, 1984

[54] CATALYST FOR USE IN THE HYDROGENOLYSIS OF METHYL GLYCOL FORMALS

[75] Inventors: Tai-Nang Huang; Carlos G. Fernandez, both of Guilford, Conn.

[73] Assignee: Olin Corporation, New Haven, Conn.

[21] Appl. No.: 479,299

[22] Filed: Mar. 28, 1983

[51] Int. Cl.$^3$ ...................... C07C 41/01; C07C 41/28
[52] U.S. Cl. .................................. 568/678; 568/613; 568/622; 568/672
[58] Field of Search ................ 568/613, 622, 672, 678

[56] References Cited

U.S. PATENT DOCUMENTS 3,972,949  8/1976  Arpe .
4,308,403 12/1981  Knifton .

FOREIGN PATENT DOCUMENTS 473097  4/1951  Canada ............................... 568/613
2900279  7/1980  Fed. Rep. of Germany .
1020500  2/1966  United Kingdom ................ 568/678

Primary Examiner—Howard T. Mars
Attorney, Agent, or Firm—Donald F. Clements; James B. Haglind

[57] ABSTRACT

The composition of and method for preparing a novel catalyst is disclosed for use in the hydrogenolysis of methyl glycol formals. The novel catalyst is prepared by impregnating a porous alumina substrate with a solution of compounds of nickel and ruthenium, and evaporating and reducing the resulting slurry to provide a substrate impregnated with a catalytic surface composition comprised of a mixture of metallic nickel and metallic ruthenium. When this catalyst is used as the catalyst in the hydrogenolysis of methyl glycol formals, improved reaction rates in the formation of the desired glycol dimethyl ether are obtained.

12 Claims, No Drawings

CATALYST FOR USE IN THE HYDROGENOLYSIS OF METHYL GLYCOL FORMALS

This invention relates to a novel catalyst having a porous alumina substrate. More particularly, this invention relates to a process for utilizing such a catalyst in the hydrogenolysis of glycol methyl formals to form glycol dimethyl ethers.

Glycol dimethyl ethers of the forumla $$CH_3O(CH_2CH_2O)_nCH_3 \qquad I$$

wherein n is an integer from 1 to 8, are used extensively in the purification of gases. Prior art techniques generally prepare these compounds by first reacting ethylene oxide with methanol to form glycol monomethyl ether. This is then reacted with formaldehyde to form a glycol monomethyl ether formal. This substance can be hydrogenated in the presence of a silica based catalyst (U.S. Pat. No. 3,972,949) to form the corresponding dimethyl ether glycol. Alternatively, the glycol monomethyl ether can be reacted with sodium to form sodium glycolate, which is reacted with methyl chloride to form the dimethyl ether glycol (U.S. Pat. No. 3,591,641). Although these processes are satisfactory for producing the desired ether glycols, there is a need to improve the reaction rate as well as the purity and the yield of the final product.

It is a primary object of this invention to provide a novel catalyst for the hydrogenolysis of formals of glycol monomethyl ether. A further object of this invention is to provide an improved process for the preparation of catalysts useful in the hydrogenolysis of formals of glycol monomethyl ethers.

Still another object of this invention is to provide an improved process for the hydrogenolysis of formals of glycol monomethyl ethers to form glycol dimethyl ethers.

These and other objects of the invention will be apparent from the following detailed description thereof.

It has now been discovered that these and other objects of the invention are accomplished with a novel hydrogenolysis catalyst prepared by impregnating porous alumina granules with solutions of compounds of nickel and ruthenium, and drying and reducing the resulting slurry to form porous alumina granules impregnated with a catalytic surface comprised of nickel metal and ruthenium metal. When the resulting novel catalyst is used in the hydrogenolysis of formals of glycol monomethyl ethers to form glycol dimethyl ethers, there is substantial improvement in the reaction rate of the process under relatively mild pressure conditions.

More in detail, the novel catalyst of this invention is a porous alumina granular substrate impregnated with a catalytic surface comprised of a mixture of nickel metal and ruthenium metal. This catalyst is preferably prepared by a solution impregnation technique, but may also be prepared by a precipitation technique, if desired.

In the solution impregnation technique, porous alumina granules having a particle size in the range from about 10 $\mu$ to about 200 $\mu$ and preferably from about 30 $\mu$ to about 80 $\mu$ are used as the catalyst base. The porosity of these granules is preferably as high as possible, and the surface area thereof generally ranges from about 80 to about 300, and preferably from about 100 to about 250 square meters per gram.

The nickel metal and ruthenium metal components of the catalyst are obtained in this technique by mixing the porous alumina granules with a solution of a nickel compound and a ruthenium compound. Suitable nickel compounds are those that are soluble in water or other solvent and include oxides, hydroxides, carbonates, nitrates, acetates and the like. Similarly suitable ruthenium compounds include those that are readily soluble in water or any solvent and include ruthenium compounds such as chlorides, bromides, and the like. The compounds may be used in anhydrous or hydrated form. Preferably nickel nitrate hexahydrate and ruthenium chloride trihydrate are utilized as the compounds from which the nickel and ruthenium metals are derived. These compounds are used not only because of their availability, but because of their cost. However, any suitable compounds may be employed. In addition, the solution of nickel compound may be applied to the porous granules separately from the solution of ruthenium compound, but it is preferred to simultaneously add the compounds of nickel and ruthenium as a single solution.

The proportion of nickel metal on the alumina granules generally ranges from about 5 to about 25 and preferably from about 8 to about 20 percent by weight of the alumina granules.

The proportion of ruthenium metal on the alumina granules generally ranges from about 0.5 to about 5 and preferably from about 1 to about 4 percent by weight of the alumina granules.

The weight ratio of nickel to ruthenium generally ranges from about 1:1 to about 50:1, and preferably from about 2:1 to about 20:1. The total weight of the mixture of nickel and ruthenium on the alumina granules ranges from about 5.5 to about 30 and preferably from about 9 to about 24 percent by weight of the alumina granules.

When utilizing the solution impregnation technique, solutions of compounds of nickel and of ruthenium are admixed in a suitable container. Generallly water is used as the solvent for the solutions, but any low boiling liquid such as methanol, ethanol and the like can be used as the solvent. Sufficient nickel compound and sufficient ruthenium compound are added to the solution in the container to provide the desired proportion of nickel metal and ruthenium metal on the alumina granules within the above defined ranges. The alumina granules are then admixed with the solutions of nickel compound and ruthenium compound to impregnate the pores of the alumina granules with the solution.

The resulting slurry is heated to remove the solvent from the slurry. When water is used as a solvent, it may be evaporated by contacting the solution with hot water or steam until the water has been evaporated and the slurry is dried. Drying is completed in a step-wise manner in which a suitable oven is heated to a temperature, for example, between about 50° and about 120° C. The resulting dry granules of alumina coated with nickel compound and ruthenium compound are then heated in the presence of hydrogen to effect reduction of the compounds of nickel and ruthenium to the metallic form. Heating is effected at a relatively high temperature, i.e., within the range between about 200° and about 500° C., and preferably between about 250° to about 450° C. The heating time may range from about 5 to about 20, and preferably from about 10 to about 15 hours.

In a preferred embodiment, heating during this reduction reaction is carried out in a series of two or more steps in which the temperature is increased in a stepwise manner. For example, the dried coated alumina granules may be heated to a temperature in the range of from about 200° to about 300° C. for about 2-4 hours, followed by heating at a temperature in the range from about 325° to about 400° C. for about 4-8 hours, followed by further heating at a temperature in the range from about 425° to about 500° C. for about 4-5 hours. Any suitable heating technique that will effect reduction of the nickel compound and the ruthenium compound without the degradation of the alumina granules to the corresponding metallic forms is suitable.

The resulting porous alumina granules impregnated and coated with the nickel metal and ruthenium metal are very effective as catalysts in the hydrogenolysis of formals of glycol methyl ethers.

If desired, the novel catalyst can be prepared from porous alumina granules by the precipitation technique or a modification technique thereof. In the precipitation technique, the porous alumina granules are added to the solution of compounds of nickel and ruthenium in the same manner as in the solution impregnation technique. However, instead of drying the resulting slurry, a suitable base such as sodium hydroxide or sodium carbonate is added to the slurry to precipitate compounds of nickel and ruthenium in the pores and on the surface of the porous alumina granules. The slurry then is preferably filtered to remove the barren solution and the resulting solids are heated to first dry and then reduce in the same manner as the dried solids contained from the solution impregnation technique.

In the modified precipitation technique, the porous alumina granules are added to a solution of a compound of either nickel or ruthenium, the metal compound is precipitated in the pores and on the surface of the porous alumina granules with a suitable base, and the solids are then separated from the barren solution. The wet solids are then added to a solution of a compound of the other metal and the resulting slurry is then processed in accordance with the solution impregnation technique. Although any of these techniques are suitable for preparing the novel catalyst of this invention, it is preferred to utilize the solution impregnation technique.

The novel catalyst of this invention is useful as a catalyst in the hydrogenolysis of formals of glycol ethers of the formula:

[CH$_3$O(CH$_2$CH$_2$O)$_n$]$_2$CH$_2$  II

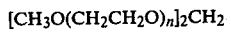

where n is in the range from about 1 to about 8 and preferably from about 1 to about 4.

In one embodiment of the invention, the formal is prepared from a glycol of the general formula:

H[O—CH$_2$CH$_2$]$_n$—OH  III

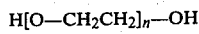

In addition, the formal may be prepared from ethers of monoethylene glycol or its homologue of the general formula:

H[O—CH$_2$—CH$_2$]$_n$O—R  IV

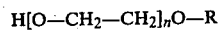

where R is an alkyl containing from about 1 to about 4 carbon atoms.

The glycols and glycol ethers are reacted with suitable formaldehyde such as paraformaldehyde in the presence of an acid such as paratoluene sulfonic acid to form a formal of Formula II. The temperature conditions for this reaction will vary depending upon the nature of the initial glycol or glycol ether. In general, the boiling point of the glycol or ether under reflux conditions at atmospheric pressure is satisfactory.

In the formal reaction, a formal of Formula II is prepared as the major product. In the process of this invention, formals of this type are conveyed to a suitable hydrogenolysis reactor comprised of a reactor containing the novel catalyst of this invention, and which is provided with a suitable feed inlet for the formal, dimethyl ether product outlet as well as an inlet means for hydrogen gas. The hydrogen gas is generally fed through a suitable gas manifold or sparger into the bottom of the hydrogenolysis reactor in countercurrent flow to the liquid formal feed. The temperature in the hydrogenolysis reactor is maintained in the range between about 150° to about 220° C., and preferably between about 180° to about 210° C.

The pressure may be varied over a wide range during the hydrogenolysis reaction and it may vary from about 15 to about 600 and preferably from about 300 to about 450 psi. The proportion of catalyst in the reactor is generally equivalent to between about 5 and about 35, and preferably between about 10 and about 25 percent by weight of the liquid content present in the reactor. Because of the stability of the novel catalyst of this invention during the hydrogenolysis reaction, the active life period of the novel catalyst is superior to conventional catalysts of this type. In addition, the reaction rate during hydrogenolysis which is achieved in the presence of the novel catalyst of this invention in the conversion of formals to dimethyl ethers is markedly improved over the reaction rate achieved with conventional cataylsts.

The dimethyl ether product stream from the hydrogenolysis reactor may contain a number of byproducts depending upon the nature of the starting formal. For example, if the starting formal is the formal of glycol monomethyl ether, then the product is comprised of glycol dimethyl ether and glycol monomethyl ether. In order to achieve separation, the product stream is distilled to separate the desired glycol dimethyl ether from the remainder of the reaction products. The remainder of the reaction products are recycled to the initial formal formation step for recycling in the process.

The following examples are presented to illustrate the invention without being limited thereby. All parts and percentages are by weight unless otherwise specified.

EXAMPLE 1

To a 2000 ml beaker, 49.2 g of Ni(NO$_3$)$_2$.6H$_2$O and 3.6 g of RuCl$_3$.3H$_2$O were added and dissolved in 200 ml of deionized water. Then 100 g of powdered alumina of surface area 190 m$^2$/g were slowly added, while stirring. After the alumina was impregnated, the resulting slurry was heated on a hot water bath at 60° C. for 2 hours. Afterwards it was dried in an oven at 110° C. overnight. The material was cooled to room temperature and packed in a glass tube. It was then heated to 250° C. under a hydrogen flow for 3 hours. Afterwards, the temperature was raised to 350° C. for another 6 hours, and then finally heated to 450° C. for 3 hours. The catalyst thus formed contained about 10% nickel and about 1.4% ruthenium.

Approximately 25 g of the catalyst were admixed with 150 g of methyl monoglycol ether formal ($CH_3OCH_2CH_2O)_2CH_2$, and placed in a 300 ml autoclave, equipped with a mechanical stirrer and agitated. Hydrogen was fed to the agitated mixture under an initial hydrogen pressure of 500 psi at a temperature of 195°–200° C. Consumption of hydrogen was shown by the drop in pressure. Both the pressure drop and reaction time were recorded, then hydrogen was refed to reach the initial pressure. The process was repeated several times until no further drop in hydrogen pressure was observed indicating the reaction was complete. The average pressure was about 400 psi. The initial reaction rate for the conversion was calculated at 4.2 mole/hour. A colorless product was obtained after removing the catalyst. Based on gas chromatographic analysis, the formal has been converted quantitatively to the dimethyl and monomethyl glycol ether at a selectivity of 100% by mole. The dimethyl glycol ether has a boiling point at 82° C. It could be separated by simple distillation from monomethyl glycol ether which has a boiling point at 130° C. The monomethyl glycol ether can be recycled to the formal preparation apparatus.

COMPARATIVE EXAMPLE A

Powdered alumina impregnated with 10% nickel metal was prepared in a similar fashion to that described in EXAMPLE 1. The $Ni/Al_2O_3$ catalyst was used in the hydrogenolysis of 150 g of monomethyl glycol ether formal under the same conditions as in EXAMPLE 1. The results showed that the reaction rate was only 0.1 mole/hour, or 42 times slower than the $Ni/Ru/Al_2O_3$ catalyst of this invention prepared and used in EXAMPLE 1, as shown on Table II.

EXAMPLES 2-7

A continuous plug flow reactor was charged with 25 g of the bimetallic catalyst $Ni-Ru/Al_2O_3$ prepared as in EXAMPLE 1. The catalyst was activated under a hydrogen flow at 200° C. for 3 hours. Monomethyl monoethylene glycol ether formal was continuously pumped through the reactor at a flow rate of about 0.25 mole per hour at 200° C. The hydrogen pressure was set at 500 psi. This example was repeated at 350, 250, 150, 75 and 25 psi and after attaining steady state, at each value, a sample of the effluent was collected and analyzed. The samples were identified as EXAMPLES 2-7, respectively.

Gas chromatography was used to analyze the effluent samples. As shown in Table 1, the conversion percentages, based on these analyses ranged from about 85 to about 92% by weight. These examples demonstrated that the catalyst maintained its high activity and selectivity under a wide range of pressure conditions.

EXAMPLES 8-10

The procedure of EXAMPLES 2-7 was repeated except that monomethyl triethylene glycol ether formal was used instead of monomethyl monoethylene glycol ether formal. In addition, only three examples were carried out at 500, 250 and 75 psi, which are identified in Table I as EXAMPLES 8-10, respectively. The conversion was at least 85% in each example.

TABLE I

Conversion of Formals Under Different Pressures* (Flow System)

| EXAMPLE | 2 | 3 | 4 | 5 | 6 | 7 |
|---|---|---|---|---|---|---|
| Pressure (psi) | 500 | 350 | 250 | 150 | 75 | 25 |
| Monomethyl Monoethylene Glycol Ether Formal | 90% | 86% | 90% | 90% | 90% | 92% |

| EXAMPLE | 8 | 9 | 10 |
|---|---|---|---|
| Monomethyl Triethylene Glycol Ether Formal | 85% | 88% | 90% |

*Catalyst charged: 25 grams of catalyst prepared as in EXAMPLE 1.
Reaction conditions: 200° C.; Flow rate of formals, 0.25 mole per hour.
No significant deactivation of catalyst was observed.

EXAMPLES 11-13

The procedure of EXAMPLE 1 was repeated using the catalyst of EXAMPLE 1 (Catalyst R) and using monomethyl diethylene glycol ether formal as the starting material in EXAMPLE 11. Similarly monomethyl triethylene glycol ether formal was used as the starting material in EXAMPLE 12, and monomethyl tetraethylene glycol ether formal was used as the starting material in EXAMPLE 13. For purposes of comparison, EXAMPLES 11, 12 and 13 were repeated, as COMPARATIVE EXAMPLES B, C, and D, respectively, wherein Catalyst R was replaced with a similarly prepared catalyst, except that only 10% nickel metal was applied to the alumina carrier. In addition, EXAMPLES 11 and 12 were repeated, as COMPARATIVE EXAMPLES E and F, respectively, in which Catalyst R was replaced with a similarly prepared catalyst except that only 2% ruthenium metal was applied to the alumina carrier. The conversion rates of the respective formals for each example is shown in Table II. A comparison of the conversion rates when novel Catalyst R is used with catalysts containing only nickel or only ruthenium shows that the conversion rate is from 3 to 42 times as rapid when novel Catalyst R is used.

EXAMPLES 14-15

EXAMPLES 1 and 11 were repeated, and identified as EXAMPLES 14 and 15, respectively, using Catalyst S comprised of porous alumina granular carrier having a surface of about 15% nickel and about 3.5% ruthenium, prepared as in EXAMPLE 1. Conversion rates for this Catalyst S were superior to those for Catalyst R and far superior to those of the COMPARATIVE EXAMPLES.

TABLE II

HYDROGENOLYSIS OF FORMALS OF MONOMETHYL GLYCOL ETHER (BATCH SYSTEM)
Conversion Rates** (mole/hour)
Example or Comparative Example in parenthesis

| Catalyst | $Ni/Al_2O_3$ | $Ru/Al_2O_3$ | R | S |
|---|---|---|---|---|
| Monomethyl glycol ether formal | 0.10 (A) | | 4.20 (1) | 4.8 (14) |
| Monomethyl diethylene glycol ether formal | 0.15 (B) | 0.075 (E) | 0.87 (11) | 0.93 (15) |
| Monomethyl triethylene glycol ether formal | 0.011 (C) | 0.012 (F) | 0.32 (12) | |
| Monomethyl tetraethylene | 0.09 | | 0.30 | |

TABLE II-continued
HYDROGENOLYSIS OF FORMALS OF MONOMETHYL
GLYCOL ETHER (BATCH SYSTEM)
Conversion Rates** (mole/hour)
Example or Comparative Example in parenthesis

| Catalyst | $Ni/Al_2O_3$ | $Ru/Al_2O_3$ | R | S |
|---|---|---|---|---|
| glycol ether formal | (D) | | (13) | |

**Catalyst charged: 25 grams of supported catalyst
Formals charged: 150 grams
Reaction Conditions: 200° C. Average reaction pressure 400 psi.
Weight percent of metals loaded on alumina:
$Ni/Al_2O_3$ = Ni 10 wt. %
$Ru/Al_2O_3$ = Ru 2 wt. %
R — Ni = 10 wt. %, Ru = 1.4 wt. %
S — Ni = 15 wt. %, Ru = 3.5 wt. %

EXAMPLE 16

Diethylene glycol was reacted with paraformaldehyde in the presence of paratoluene sulfonic acid to produce diethylene glycol formal. A mixture containing 25 g of alumina supported nickel-ruthenium catalyst prepared as in EXAMPLE 1 and 150 g of diethylene glycol formal was added to a 300 ml autoclave, equipped with a mechanical stirrer. Initial conditions were hydrogen pressure, 450 psi; and temperature 200° C. Consumption of hydrogen was noticed by the drop in pressure. As the hydrogenolysis reaction proceeded, the pressure drop was recorded. Hydrogen was then refed to reach the initial pressure of 450 psi. The process was repeated several times until no further absorption of hydrogen was observed. This indicated that the reaction was complete. The initial reaction rate for the conversion was calculated at 0.394 mole/hour. A colorless product was obtained after filtering off the catalyst. Based on gas chromatographic analysis, the original diethylene glycol formal had been converted to a mixture of diethylene glycol monomethyl ether, diethylene glycol dimethyl ether and diethylene glycol. Analysis showed that there was 100% conversion of the diethylene glycol formal. The molar ratio of the various components of the hydrogenolysis product was found to be 0.76 mole of monomethyl diethylene glycol, 0.25 mole of diethylene glycol dimethyl ether and 0.25 mole of diethylene glycol.

EXAMPLE 17

Triethylene glycol formal was prepared by reacting triethylene glycol and paraformaldehyde in the presence of traces of paratoluene sulfonic acid. A continuous plug flow reactor was charged with 25 g of the alumina supported nickel-ruthenium catalyst prepared as in EXAMPLE 1, which was then activated under a hydrogen flow at 200° C. for 3 hours. Triethylene glycol formal was continuously pumped through the reactor at a flow rate of 0.25 mole per hour at 200° C. The hydrogen pressure was set at 350 psi. After attaining steady state, a sample of the effluent was collected and analyzed. Gas chromatography was used to analyze the effluent samples. The conversion percentages at different reaction pressures, based on the gas chromatographic analysis, remained at approximately 80%. The molar ratio of the components of the reaction product were found to be 3 moles of monomethyl triethylene glycol ether to 1 mole of triethylene glycol dimethyl ether and to 1 mole of triethylene glycol.

What is claimed is:

1. In the process for preparing glycol alkyl ethers from the corresponding glycol formals by hydrogenolysis in the presence of a catalyst, the improvement which comprises employing as said catalyst a hydrogenolysis catalyst comprised of alumina granules having a porous catalytic surface, said surface being impregnated with a mixture comprised of nickel and ruthenium wherein the weight of said mixture ranges from between about 5.5 to about 30 percent of the weight of said alumina granules, and wherein the proportion of catalyst is between about 5 and about 35 percent by weight of the liquid content present in the reactor.

2. The process of claim 1 wherein said hydrogenolysis reaction is carried out in the liquid phase at a pressure in the range of from about 15 to about 600 psi.

3. The process of claim 2 wherein said hydrogenolysis reaction is carried out at a temperature in the range of from about 150° to about 220° C.

4. The process of claim 1 wherein said glycol alkyl ether is a mixture of glycol monomethyl ether and glycol dimethyl ether.

5. The process of claim 1 wherein said formal is methyl monoglycol ether formal.

6. The process of claim 3 wherein said pressure is in the range of from about 300 to about 450 psi.

7. The process of claim 6 wherein said temperature is in the range of from about 180° to about 210° C.

8. The process of claim 1 wherein the proportion of said catalyst is between about 10 and about 25 percent by weight.

9. The process of claim 1 wherein the total weight of said mixture ranges from between about 9 and about 24 percent by weight of said alumina granules.

10. The process of claim 1 wherein the weight ratio of nickel to ruthenium in said surface is in the range from between about 2:1 to about 20:1.

11. The process of claim 1 wherein the proportion of nickel on said catalyst ranges from about 8 to about 20 percent by weight of the alumina granules.

12. The process of claim 1 wherein the proportion of said ruthenium on said catalyst ranges from about 1 to about 4 percent by weight of said alumina granules.

* * * * *